United States Patent
Gunn et al.

(10) Patent No.: US 6,939,976 B2
(45) Date of Patent: Sep. 6, 2005

(54) PROCESS FOR MAKING ALLYL SUCCINIC ANHYDRIDE

(75) Inventors: Euen Gunn, Trenton, NJ (US);
Jean-Christophe Galland, Lyons (FR);
Blaise Didillon, Franchville (FR);
Thomas Delacroix, Lyons (FR)

(73) Assignee: Rhodia Inc., Cranbury, NJ (US)

( * ) Notice: Subject to any disclaimer, the term of this patent is extended or adjusted under 35 U.S.C. 154(b) by 115 days.

(21) Appl. No.: 10/822,237

(22) Filed: Apr. 9, 2004

(65) Prior Publication Data

US 2004/0220414 A1 Nov. 4, 2004

Related U.S. Application Data

(60) Provisional application No. 60/461,878, filed on Apr. 10, 2003.

(51) Int. Cl.[7] .............................................. C07D 307/60
(52) U.S. Cl. ..................................................... 549/255
(58) Field of Search ......................................... 549/255

(56) References Cited

U.S. PATENT DOCUMENTS

| 2,297,039 | A | 9/1942 | van Melsen |
| 3,243,480 | A | 3/1966 | Anderson et al. ........... 260/369 |
| 3,819,660 | A | 6/1974 | Cahill et al. ........... 260/346.8 R |
| 4,317,744 | A | 3/1982 | Levi ........................... 252/389 |

OTHER PUBLICATIONS

Phillips et al., "Polynuclear Aromatic Hydrocarbons. VIII[1] The Reaction Between Allylsuccinic Anhydride and Benzene," J. Am. Chem. Soc., vol. 80 (1958), 3663–3667.

Barry B. Snider, "Lewis–Acid–Catalyzed Ene Reactions," Acc. Chem. Res., (1980), 13, pp. 426–432.

Alder et al., Uber die Anlagerung von Maleinsäure–anhydrid und Azodicarbon–säure–ester an einfach ungesättigte Kohlenwasserstoffe. Zur Kenntnis von Substitutionsvorgängen in der Allyl–Stellung, Chemische Berichte, 1943, vol. 76, pp. 27–53.

*Primary Examiner*—Bernard Dentz

(57) ABSTRACT

A process for the production of allyl succinic anhydride comprising reacting a mixture of propene with maleic anhydride in the presence of a catalyst comprised of an alkyl tin chloride as provided. The process can be run efficiently at temperatures below about 200° C. without and the formation of polymer or decomposition by-products.

14 Claims, No Drawings

PROCESS FOR MAKING ALLYL SUCCINIC ANHYDRIDE

CROSS-REFERENCE TO RELATED APPLICATIONS

This application claims priority from U.S. provisional patent application No. 60/461,878 filed Apr. 10, 2003.

FIELD OF THE INVENTION

This invention relates a process for making allyl succinic anhydride.

BACKGROUND OF THE INVENTION

Allylsuccinic anhydride can be made by a Lewis Acid catalyzed ene reaction between maleic anhydride and propene according to reaction scheme 1 below:

Reaction Scheme 1

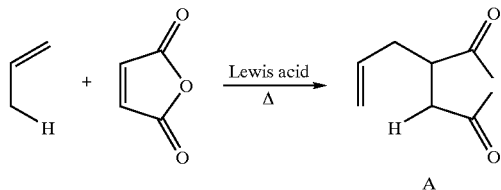

$AlCl_3$ catalyzes the reaction efficiently but requires harsh conditions (T=200° C.). However, the anhydride undergoes exothermic polymerization at 205° C. For safety reasons, the industrial process should be performed 30° C. below the polymerization reaction. However, in these conditions, $AlCl_3$ is not an efficient catalyst.

The ene reaction is the reaction of an alkene having an allylic hydrogen (ene) with a compound containing a double or triple bond (enophile) to form a new bond with migration of the ene double bond and 1,5-hydrogen shift.

Since the enophile, like the dienophile in a Diels-Alder reaction, should be electron deficient, complexation of Lewis acids to enophile containing basic groups promotes the ene reaction. See Snider, B. B. *Acc. Chem. Res.* 1980, 13, 426. The choice of the Lewis acid depends upon the enophile to be used. Some of them require very acidic Lewis acids, others require milder ones. Some examples of Lewis used for the ene reactions are: $AlCl_3$, $EtAlCl_2$, $Me_2AlCl$, $BF_3$, $SnCl_4$, $TiCl_4$, $FeCl_3$, $ZnCl_2$.

In the literature, the ene reaction between propene and maleic anhydride is described without catalyst but at a high temperature (200–250° C.). See (a) Alder, K.; Pasher, F.; Schmitz, A. *Chem. Ber.* 1943, 76, 27. (b) Phillips, D. D.; Hill, T. J. *J. Am. Chem. Soc.* 1958, 80, 3663. (c) Anderson, et al., 1966, U.S. Pat. No. 3,243,480.

U.S. Pat. No. 3,819,660 discloses the reaction of an alkene such as propene with maleic anhydride to produce an alkenyl succinic anhydride. That patent teaches the use of a mixture of para-toluene sulfonic acid and acetic anhydride as a catalyst.

SUMMARY OF THE INVENTION

This invention is directed to a process for making allyl succinic anhydride, comprising reacting propene with maleic anhydride in the presence of a catalytic amount of alkyl tin chloride catalyst.

DETAILED DESCRIPTION OF THE INVENTION

The term "catalytic amount" is recognized in the art and means a substoichiometric amount of catalyst relative to a reactant. As used herein, a catalytic amount is typically in the range of from about $1.0 \times 10^{-6}$ to about 0.9 mole catalyst per mole of maleic anhydride.

The catalysts useful in the process of the present invention are organotin chloride catalysts. Suitable organotin chloride catalysts are those according to formula (1) below:

wherein $R^1$, $R^2$ are each independently alkyl, alkenyl, alkynyl, or phenyl, $R^3$ is Cl or alkyl, alkenyl, or alkynyl.

As used herein, "alkyl" means a saturated hydrocarbon, including, straight or branched saturated hydrocarbon chains such as methyl ethyl, propyl, 1-methylethyl, butyl, 1-methylpropyl, 1,1-dimethylethyl, hexyl, octyl, decyl, dodecyl, stearyl, and saturated hydrocarbon rings, such as cyclohexyl and cyclooctyl. As used herein, "alkenyl" means a straight or branched hydrocarbon chain having one or more carbon-carbon double bonds, such as for example, ethene, propene, 1-butene, 2-butene, propadiene. As used herein, "alkynyl" means a straight of branched hydrocarbon chain having one or more carbon-carbon triple bonds, such as, for example, ethyne, propyne, butadiyne, 1,4-hexadiyne. As used herein, "phenyl" means an aromatic ring of six carbon atoms, which may optionally be substituted on one or more carbons of the ring with hydrocarbon groups, including, for example, alkyl, alkenyl, and alkynyl groups In one embodiment, $R^1$ and $R^2$ are each independently ($C_1$–$C_6$)alkyl or phenyl and $R^3$ is Cl or ($C_1$–$C_6$)alkyl. As used herein, "($C_1$–$C_6$) alkyl" means a straight or branched alkyl group having from 1 to 6 carbon atoms per group, such as, for example, methyl, ethyl, propyl, 1-methylethyl, butyl, 1-methylpropyl, 1,1-dimethylethyl, 2,2-dimethylpropyl, 1,1-dimethylpropyl, or hexyl, 4-methylpentyl.

Suitable organotin chloride catalysts include methyl tin dichloride, dimethyl tin dichloride, ethyl tin dichloride, diethyl tin dichloride, n-butyl tin trichloride, di-n-butyl tin dichloride, s-butyl tin dichloride, di s-butyl tin dichloride, t-butyl tin dichloride, di t-butyl tin dichloride, n-pentyl tin trichloride, di n-pentyl tin dichloride, n-hexyl tin trichloride, di n-hexyl tin dichloride and phenyl tin dichloride.

The process of the present invention is useful at temperatures below the temperature at which competing reactions, such as polymerization reactions and/or decomposition reactions, become problematic. In one embodiment, the reaction according to the process of the present invention is carried out at temperatures below about 200° C., more typically below about 180° C., and even more typically from about 155° C. to about 175° C.

In one embodiment, the reaction mixture initially comprises substantially equimolar amounts propene and maleic anhydride. In an alternative embodiment, the reaction mixture initially comprises a molar excess, typically up to about 10 mole %, of propene relative to the amount of maleic anhydride.

The reaction is typically carried out in a solvent such as, for example, a hydrocarbon, more typically an aromatic hydrocarbon such as toluene, that is, inert under the anticipated reaction conditions. The amount of solvent may vary widely. An amount of from about 0.1 to about 10 parts by weight ("pbw") solvent per pbw maleic anhydride is typically used. More typically an amount of from about 0.5 to about 1.5 pbw solvent per pbw maleic anhydride is used.

In one embodiment, the process of the present invention is conducted at a pressure of from about 100 to about 10,000 pounds per square inch above atmospheric pressure ("psig"), typically from about 100 to about 1,000 psig, and more typically from about 100 to about 800 psig.

The reaction is typically carried out in the presence of a free radical scavenger, such as, for example, methoxyphenol, to inhibit polymerization of the maleic anhydride reactant and the allyl succinic product.

The allyl succinic anhydride product is useful for a variety of purposes, such as for example, as a corrosion inhibitor. Homopolymers and copolymers of a similar monomer are known to those skilled in the art to be useful in corrosion inhibitors, as disclosed in U.S. Pat. No. 4,317,744 to Levi entitled "Corrosion Inhibitors".

In one embodiment, the ally succinic anhydride is used to form a hydrosilylated diacid product according to Reaction Scheme 2 below, wherein the ally succinic anhydride is grafted to a silicone oil via a hydrosilylation reaction and hydrosilylation product is then hydrolysed to form a diacid product. The diacid product is useful as a corrosion inhibitor.

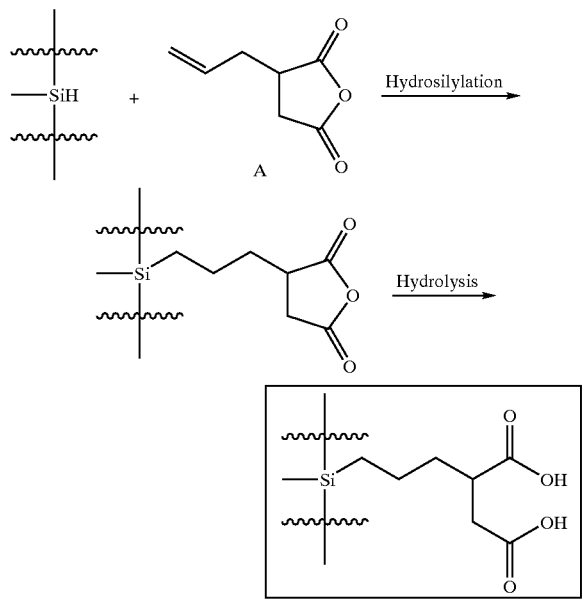

Reaction Scheme 2

The hydrosilylated diacid product is useful as a corrosion inhibitor

EXAMPLE 1

A screening of Lewis acids as catalysts for the ene reaction was performed in a Top reactor (25 mL). Maleic anhydride, methoxyphenol (polymerization inhibitor), Lewis acid and solvent (anhydrous toluene) were introduced under argon into the reactor. Then, the reactor was cooled in dry ice/acetone bath and the propene was added. The relative amounts of the materials used are given in the following table.

| Reactant | MW (g/mol) | Eq. | n (mmol) | m (g) |
|---|---|---|---|---|
| Maleic anhydride | 98.06 | 1 | 41 | 4 |
| 4-Methoxyphenol | 124.14 | 0.02 | 0.8 | 0.1 |
| Lewis acid | | 0.05 | 2 | |
| Propene | 42.08 | 2.3 | 95 | 4 |
| Toluene | | | | 4 mL |

The reaction mixture was stirred for 12 hours at a given temperature. Finally, the reaction mixture was analyzed by IR spectroscopy.

First, the reaction conditions and the qualitative IR method were validated by a reference experiment with $AlCl_3$ as a catalyst at 200° C. Then, a screening of the 38 typical Lewis acids listed below (wherein "acac" means acetyl acetonate) as the catalyst for the reaction was conducted using the same procedure, except at a temperature of 150° C.

| | | | |
|---|---|---|---|
| $AlBr_3$ | $Co(acac)_3$ | $K_2PO_4$ | $Ti(OiPr)_4$ |
| $AlCl_3$ | CsCl | Mn(phtalocyanin) | $TiCl_4$ |
| $AlCl_3/CsCl$ | $Cu(acac)_2$ | $Mo(C_5H_5)_2Cl_2$ | $Ti(C_5H_5)_2Cl_2$ |
| $AlCl_3/NaCl$ | CuCl | $NbOCl_2$ | $V(C_5H_5)_2Cl_2$ |
| $AlI_3$ | $DyCl_3$ | $Nd(Otf)_3$ | $WCl_4$ |
| $AlMe_3$ | $Fe(acac)_2$ | $Ni(acac)_2$ | $Zr(C_5H_5)_2HCl$ |
| $AsPh_3$ | $FeCl_3$ | $Rh(TFA)_2$ | $Zr(C_5H_5)_2Cl_2$ |
| $BBr_3$ | $Fe(C_5H_5)_2$ | $SePh_2Cl_2$ | $ZnF_2$ |
| $B(amyl)_3$ | $GeI_4$ | $SnBuCl_3$ | |

The IR spectra demonstrated that none of the reactions at 150° C. using the Lewis acid compounds produced the desired product.

$AlCl_3$, $HfCl_3$, $ZrCl_2$, $CdI_2$, and $Me_2SnCl_2$ were then tested at 200° C. $HfCl_3$ and $ZrCl_2$ did not give the expected product, whereas in the presence of $Me_2SnCl_2$ or $CdI_2$, the product is observed by IR spectroscopy. But as mentioned before, this temperature is likely too high for an industrial process.

Then, a targeted screening of tin compounds was performed at 175° C. The results are given in the following table (+:product; −: no product):

| Catalyst | IR qualitative result |
|---|---|
| $Me_2SnCl_2$ | +++ |
| $n-Bu_2SnCl_2$ | ++ |
| $n-BuSnCl_3$ | + |
| $SnCl_4$ | − |
| $Ph_3SnCl$ | − |

The three catalysts $Me_2SnCl_2$, $n-BuSnCl_2$ and $n-BuSnCl_3$ were active in the formation of the allylsuccinic anhydride. $Me_2SnCl_2$ was the most efficient.

Considering these results, we may consider that an efficient catalyst for this reaction should have intermediary acidity. Thus, the acidity of tin Lewis acids has been evaluated by calculating their respective Lowest Unoccupied Molecular Orbital ("LUMO") energies

| Tin compound | E Lumo | Activity |
|---|---|---|
| Tin tetrachloride | −96.16 | Inactive |
| n-butyl tin trichloride | −71.2 | Active |
| Diphenyl tin dichloride | −51.81 | Not tested |
| Divinyl tin dichloride | −51.04 | Not tested |
| Dimethyl tin dichloride | −50.12 | Active |
| Di n-butyl tin dichloride | −48.74 | Active |
| Di t-butyl tin dichloride | −48.37 | Not tested |
| Triphenyl tin chloride | −28.52 | Inactive |

The results suggest a relationship between catalytic activity and LUMO energy of the compounds. The three active Lewis acids tested each have a LUMO energy between −40 and −80 kcal/mol, whereas neither a stronger Lewis acid ($SnCl_4$, $E_{LUMO}$=−96.16 kcal/mol), nor a weaker Lewis acid ($Ph_3SnCl$, $E_{LUMO}$=−28.52 kcal/mol) catalyzed the ene reaction.

EXAMPLE 2

A Parr reactor (2L) was charged with 300 g maleic anhydride (3.06 moles), 300 g toluene, 10 g dimethyl tin dichloride, and 138 g propene (1.1 molar equivalents, based on maleic anhydride). The temperature of the reaction mixture was increased to 175° C. At this temperature the pressure within the reactor was 634 psig. The reaction mixture was stirred at 200 rpm with a gassing stirrer. The pressure dropped substantially linearly through the reaction, indicating propene consumption. After 48 hours of heating, the pressure within the reactor was 412 psi.

The reaction mixture was cooled to yield a clean, polymer free liquid. Solvent was removed using a rotary evaporator to provide a liquid product comprising of 59% maleic anhydride, and 41% allylsuccinic anhydride (by NMR).

What is claimed is:

1. A process for the production of allyl succinic anhydride, comprising reacting propene with maleic anhydride in the presence of a catalytically effective amount of an organotin chloride catalyst.

2. The process of claim 1, wherein the organotin chloride catalysts are those according to formula (1) below:

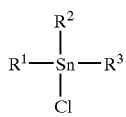

(1)

wherein $R^1$, $R^2$ are each independently alkyl, alkenyl, alkynyl, or phenyl, $R^3$ is Cl or alkyl, alkenyl, or alkynyl.

3. The process of claim 2, wherein $R^1$ and $R^2$ are each independently ($C_1$–$C_6$)alkyl or phenyl and $R^3$ is Cl or ($C_1$–$C_6$)alkyl.

4. The process of claim 1, wherein the catalyst comprises one or more compound selected from the group consisting of methyl tin dichloride, dimethyl tin dichloride, ethyl tin dichloride, diethyl tin dichloride, n-butyl tin trichloride, di-n-butyl tin dichloride, s-butyl tin dichloride, di s-butyl tin dichloride, t-butyl tin dichloride, di t-butyl tin dichloride, n-pentyl tin trichloride, di n-pentyl tin dichloride, n-hexyl tin trichloride, di n-hexyl tin dichloride, and phenyl tin dichloride.

5. The process of claim 1 wherein the catalyst comprises one or more compound selected from the group consisting of n-butyl tin trichloride, diphenyl tin dichloride, divinyl tin dichloride, dimethyl tin dichloride, di n-butyl tin dichloride, and di t-butyl tin dichloride.

6. The process of claim 1 wherein said catalyst comprises one or more compound selected from the group consisting of dimethyl tin dichloride, dibutyl tin dichloride, and butyl tin trichloride.

7. The process of claim 1 wherein the reaction is conducted at a temperature of less than about 200° C.

8. The process of claim 1 where the mixture conducted at a temperature of less than about 180° C.

9. The process of claim 1, wherein the reaction mixture initially comprises substantially equimolar amounts propene and maleic anhydride.

10. The process of claim 1, wherein the reaction mixture initially comprises a molar excess of propene relative to the amount of maleic anhydride.

11. The process of claim 1, the reaction mixture initially comprises a molar excess, of up to about 10 mole %, of propene relative to the amount of maleic anhydride.

12. The process of claim 1, wherein the process is carried out in a hydrocarbon solvent.

13. The process of claim 1, wherein the process is conducted at a pressure of from about 100 to about 10,000 pounds per square inch above atmospheric pressure.

14. The process of claim 1, wherein the process is conducted in the presence of a free radical scavenger.

* * * * *